United States Patent [19]

Akiyama

[11] Patent Number: 4,622,469

[45] Date of Patent: Nov. 11, 1986

[54] METHOD FOR DETECTING ROTTEN ALBUMEN AND APPARATUS THEREFOR

[75] Inventor: Hirokazu Akiyama, Zushi, Japan

[73] Assignee: Q. P. Corporation, Tokyo, Japan

[21] Appl. No.: 706,425

[22] Filed: Feb. 27, 1985

[51] Int. Cl.$^4$ ............................................. G01N 21/64
[52] U.S. Cl. .............................. 250/458.1; 250/461.1
[58] Field of Search .......................... 250/458.1, 461.1; 356/417, 407

[56] References Cited

FOREIGN PATENT DOCUMENTS 58-92933  6/1983  Japan ................................. 250/461.1

OTHER PUBLICATIONS

Toshiba publication entitled, "Color Filter Glass", F3924, pp. 1-10.

Primary Examiner—Janice A. Howell
Attorney, Agent, or Firm—Pollock, VandeSande & Priddy

[57] ABSTRACT

A method and an apparatus for detecting rotten albumen in broken raw eggs which may include sound yolk are disclosed. The apparatus includes a device for casting ultraviolet light onto the albumen, an optical filter system filtering a complex of fluorescence of the albumen and the yolk and an ultraviolet light reflected from or transmitted through the albumen so as to transmit only the components due to fluorescence of the albumen, and a discriminator which compares the level of a signal corresponding to the fluorescence of the albumen to a threshold level corresponding to the fluorescence of the sound albumen. The method and the apparatus are applicable to both separating-type and nonseparating-type automatic egg breakers.

11 Claims, 6 Drawing Figures

METHOD FOR DETECTING ROTTEN ALBUMEN AND APPARATUS THEREFOR

BACKGROUND OF THE INVENTION

1. Field of the Invention

This invention relates to a method for detecting rotten albumen and an apparatus therefor and more particularly to an optical method for recognizing rotten albumen in raw eggs and an apparatus therefor employing an optical filter.

2. Description of the Prior Art

Generally, production of processed egg products, e.g., mayonnaise requires a step of removing rotten albumen.

A recently developed system casts a beam of ultraviolet light with a wavelength in the range of about 300 to 410 nm and a peak intensity at about 365 nm onto the albumen of a broken raw egg and recognizes rotten albumen by checking for the presence of strong fluorescence from the rotten albumen.

As shown in FIG. 1, this system comprises an ultraviolet transmitter, not shown, a converging lens 1, an optical filter 2, a photoelectronic receiver 3, an amplifier 4 for an electrical output of the photoelectronic receiver 3, and a discriminating means, not shown, for recognizing whether or not the albumen is rotten.

Under the incident ultraviolet light, sound albumen produces only an extremely weak light-blue fluorescence while rotten albumen produces a strong, blue or green fluorescence due to the presence of the fluorescent material-producing fungi pseudomonas in the rotten albumen. The converging lens 1 receives the complex of the fluorescence and reflected ultraviolet light from the albumen under inspection and sends it to the optical filter 2. The optical filter 2 filters out ultraviolet light at wavelengths less than 400 nm and transmits the resulting fluorescence component to the photoelectronic receiver 3. In practice, a combination of tinted glass filters, e.g., L-42, Y-43, Y-44 and G-55 (JIS), all of which are trademarks of Toshiba Glass Co., Ltd., serve as the optical filter 2. The photoelectronic receiver 3 cuts off the fluorescence components at wavelengths exceeding 700 nm due to its optical properties thus passing only visible fluorescence components. GaAsP photodiodes are used as the photoelectronic receiver 3. The output of the photoelectronic receiver 3 is sent through the amplifier 4 to the discriminating means which compares the received signal level to an electrical reference level in correspondence to a predetermined threshold level of fluorescence from sound albumen and outputs a signal indicating the presence or absence of rotten albumen.

FIG. 2 shows the spectral transmissivity of the above-described optical filter 2 at a curve I, the relative sensitivity of the above-described photoelectronic receiver 3 at a curve II, the relative intensity of the fluorescence of rotten albumen at a curve III and the relative intensity of the fluorescence of sound yolk at a curve IV. The wavelength range of the curve III is almost fully contained within the range delimited by the curves I and II. The peak of the curve III falls at about 463 nm wavelength, almost coincident with the rising edge of curve I. Thus, the optical filter 3 isolates the low-wavelength end of the fluorescence spectrum with high efficiency and specificity.

However, the curves III and IV overlap in the range of abut 500 to 600 nm, especially about 520 to 570 nm. It is impossible to resolve rotten albumen if the threshold level segregating sound and rotten albumen should be set to a level, e.g. 50%, within the range of intensity due to fluorescence from the yolk. Thus this prior art system is not applicable to nonseparating-type automatic egg breakers which do not separate albumen from yolk. In addition, this prior art system could mistake sound albumen for rotten albumen in case of inadvertent admixture of sound yolk by a malfunctioning separating-type automatic egg breaker.

SUMMARY OF THE INVENTION

An object of this invention is to provide a method for detecting rotten albumen applicable to raw eggs which may include sound yolk.

In order to accomplish this object, the method of this invention comprises the steps of casting untraviolet light onto albumen under inspection which may include sound yolk, filtering the complex of fluorescence from the albumen and the sound yolk and reflected untraviolet light from the albumen and transmit only the fluorescence components from the albumen, comparing the level of a signal corresponding to the intensity of the received fluorescence to a threshold level corresponding to the fluorescence from sound albumen.

Another object of this invention is to provide an apparatus for detecting rotten albumen applicable to both separating-type and nonseparating-type egg breakers.

In order to accomplish this object, the apparatus of this invention comprises an ultraviolet light transmitter, means for filtering a complex of fluorescence from albumen and sound yolk and ultraviolet light reflected from or transmitted by the albumen so as to transmit only the fluorescence from the albumen, and a discriminator capable of comparing the level of a signal corresponding to the intensity of received fluorescence to threshold level corresponding to the fluorescence from sound albumen. The filtering means may be an optical filter system consisting of a tinted glass filter and an interference filter.

DESCRIPTION OF THE PREFERRED EMBODIMENTS

Figure 1:
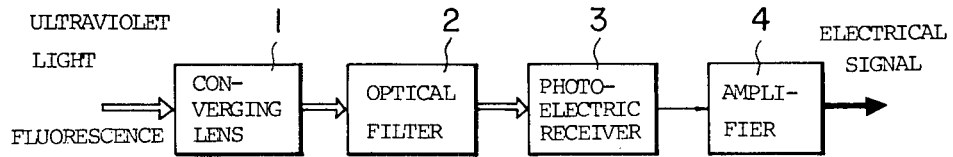
FIG. 1 is a block diagram of prior art fluorescence sensor.
Figure 2:
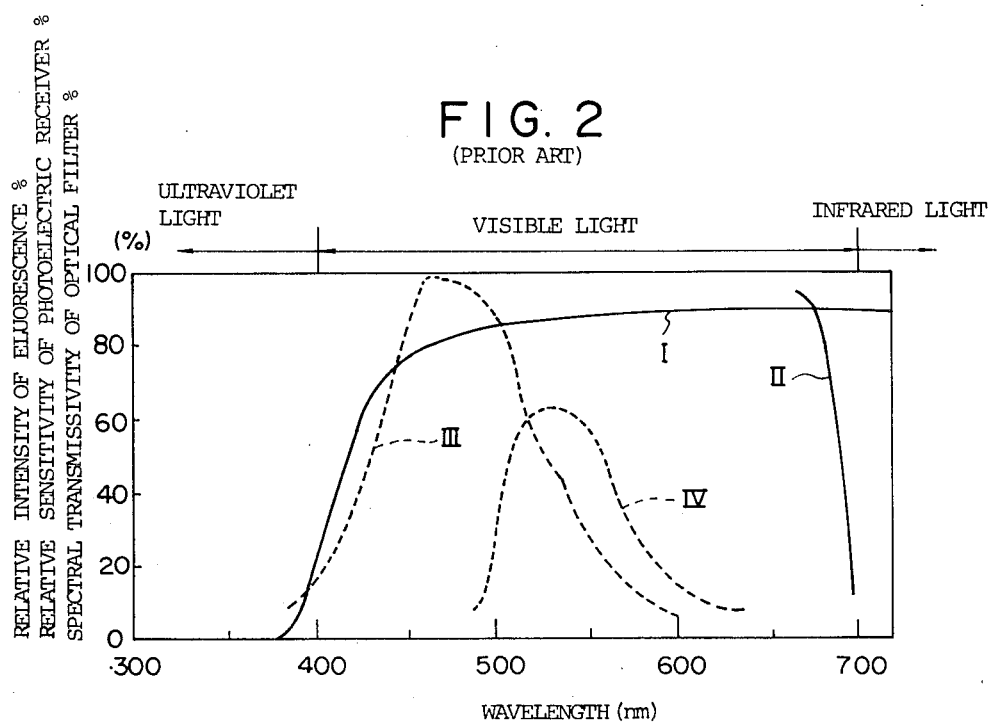
FIG. 2 is a graph representative of the spectral transmissivity of an optical filter of the prior art, the relative sensitivity of a photoelectronic receiver, the relative intensity of the fluorescence of rotten albumen and the relative intensity of the fluorescence of sound yolk.

The preferred embodiments of this invention will be described with reference to FIGS. 3 to 6. Elements similar to those of the prior art system of FIG. 1 will be labelled with the same reference numerals.

Figure 3:
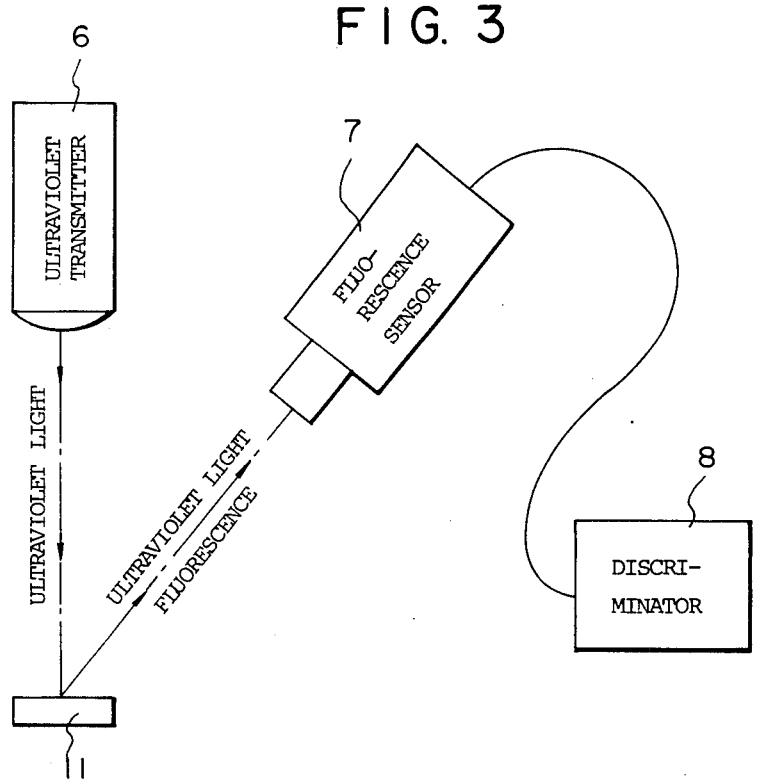
FIG. 3 is a schematic diagram representative of a rotten albumen detecting apparatus according to this invention.
Figure 4:
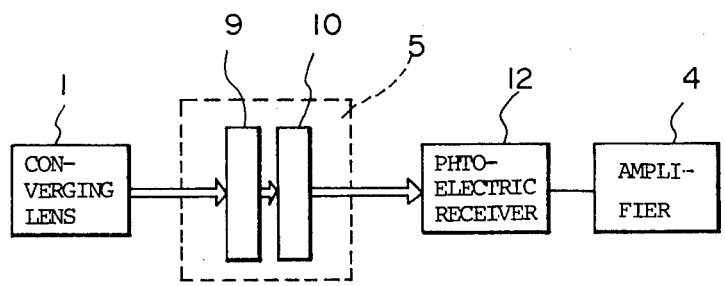
FIG. 4 is a block diagram of the fluorescence sensor of FIG. 3.

A rotten albumen detecting apparatus of this invention, as shown in FIG. 3, comprises an ultraviolet transmitter 6, a fluorescence sensor 7 and a discriminator 8. The ultraviolet transmitter 6 casts a beam of ultraviolet light at wavelengths of about 300 to 410 nm onto the albumen 11 of a broken raw egg under inspection, which may include sound yolk. The intensity of this ultraviolet light beam may be at 365 nm. The fluorescence sensor 7, as shown in FIG. 4, comprises a converging lens 1, an optical filter system 5, a photoelectronic receiver 12 such as a phototransistor, and an amplifier 4. The photoelectronic receiver 12 receives only visible-light fluorescence at wavelengths of about 400 to 500 nm from the optical filter system 5. The discriminator 8 comprises a comparator, which compares the electrical output from the amplifier 4 with an electrical reference level corresponding to a predetermined threshold level between the fluorescence intensities of sound and rotten albumen and outputs a signal indicating the presence or absence of rotten albumen.

The system according to this invention can distinguish rotten albumen from both sound albumen and yolk due to the effect of the optical filter system 5. The optical filter system 5 comprises the combination of a first filter element 9 and a second filter element 10. The first filter element 9 is similar to the optical filter 2 of FIG. 1. The second filter element 10 is a sort of transmissive interference filter. The upper limit of the pass band of the second filter element 10 is about 500 nm. The second filter element 10 is composed of a laminate of multiple layers of dielectric substances formed on the transmission surface of the first filter element 9 by means of vacuum deposition. For example, the multiple layers may be superposed layers of titanium dioxide ($TiO_2$) and silicon dioxide ($SiO_2$). The respective refractive indexes of $TiO_2$ and $SiO_2$ are 2.30 and 1.46. The thickness of the laminate overall is 1.5 $\mu$m. Twenty layers tens of nanometers thick constitute the laminate. The vacuum deposition is carried out at 360° C. under vacuum at a pressure of 1.33 mP ($10^{-5}$ Torr). The cut-off wavelength of the second filter element 10 is determined by the thicknesses and/or the indices of refraction of the layers.

Figure 5:
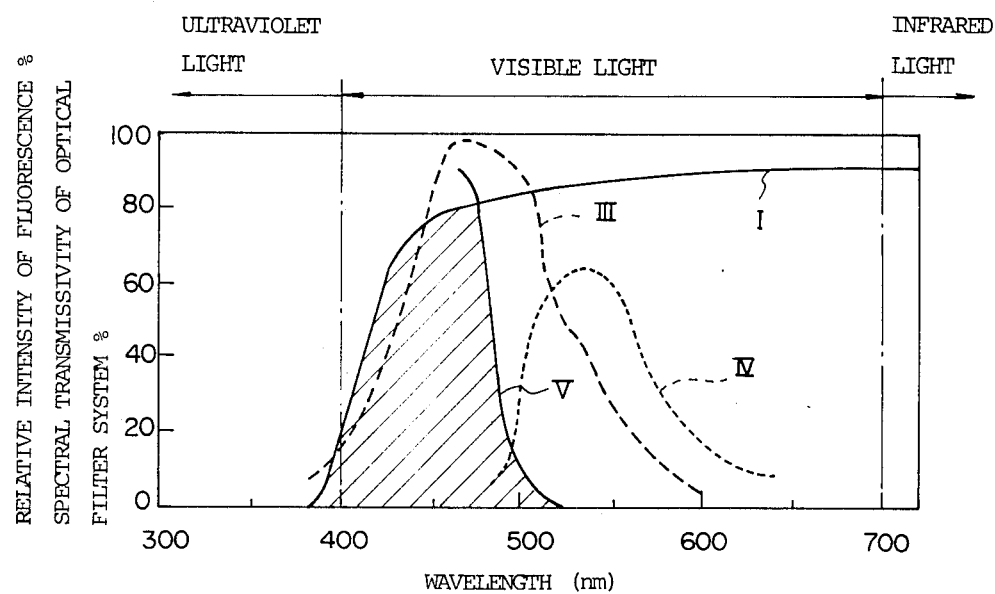
FIG. 5 is a graph representative of the spectral transmissivity of an optical filter system of this invention, the relative intensity of the fluorescence of rotten albumen and the relative intensity of the fluorescence of sound yolk.

The curve V in FIG. 5 illustrates the effect of the transmission properties of the second filter element 10. The hatched area in FIG. 5 represents the transmission properties of the optical filter system 5, the pass band of which lies between about the upper limit of wavelength of ultraviolet light, i.e. about 400 nm and about the lower limit of wavelength of fluorescence from sound yolk, i.e. about 500 nm so as to effectively exclude all components due to fluorescence of sound yolk.

Figure 6:
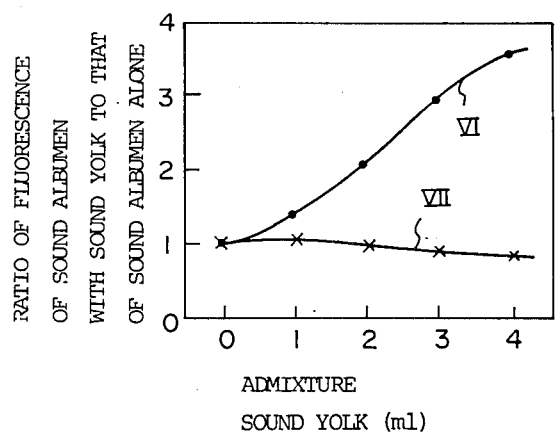
FIG. 6 is a graph representative of the relationship between the amount of sound yolk admixed into the albumen and the ratio of fluorescence of a mixture of sound albumen and admixed sound yolk to that of sound albumen alone.

FIG. 6 illustrates the relationship between the amount of sound yolk inadvertently mixed into the albumen of one egg and the ratio of the intensity of filtered fluorescence received by the receiver 12 from the mixture of sound albumen and sound yolk to that from sound albumen alone for both the prior art and this invention. The prior art optical filter 2 and the first filter element 9 of this invention are both L-42 tinted glass filters. In FIG. 6, the X-axis represents an admixed amount of sound yolk in a single egg white and the Y-axis represents the ratio of fluorescence intensity of sound albumen plus sound yolk versus sound albumen alone. The curves VI and VII represent the respective ratios for the prior art and this invention. As is apparent from FIG. 6, the prior art ratio increases with the admixture of sound yolk and on the other hand, the ratio for this invention is substantially constant.

What is claimed is:

1. An apparatus for detecting rotten albumen in raw egg, comprising:
   means for casting ultraviolet light onto albumen to be inspected, the albumen may include yolk material;
   means for filtering a complex of fluorescence received from the albumen and ultraviolet light reflected from or transmitted through the albumen, the filtering means transmitting only the fluorescence component from the albumen; and the filtering means further including an optical filter system having a first filter element and a second filter element, the first filter element being a tinted glass filter and the second filter element being an interference filter;
   a photoelectric receiver working cooperatively with the filtering means for receiving the fluorescence of the albumen and outputting a corresponding electrical signal;
   means connected electrically to the photoelectric receiver for comparing the outputted electrical signal with a reference signal, the outputted signal corresponding to the level of received fluorescence of albumen and the reference signal corresponding to a threshold level representing the fluorescence of sound albumen.

2. An apparatus as recited in claim 1, wherein the interference filter is in the form of a laminate of light-transmissive dielectric substances and is formed on an optically active surface of the tinted glass filter.

3. An apparatus as recited in claim 2, wherein the laminate is about 1.5 $\mu$m thick and comprises 10 layers of titanium dioxide and 10 layers of silicon dioxide superimposed alternate.

4. An apparatus as recited in claim 2, wherein the laminate is about 1.5 $\mu$m thick overall and comprises about 10 layers of a light-transmissive dielectric substance with a refractive index of about 2.30 and about 10 layers of a light-transmissive dielectric substance with a refractive index of about 1.46 superimposed alternate.

5. An apparatus as recited in claim 2, wherein said optically active surface of the tinted glass filter is the final emission surface.

6. An apparatus as recited in claim 1, wherein the pass band of said filtering means is from about 420 to 500 $\mu$m.

7. An apparatus as recited in claim 1, wherein the threshold level lies at about 50% of the peak fluorescence of rotten albumen.

8. An apparatus as recited in claim 1, wherein said ultraviolet light casting means casts ultraviolet light onto the albumen of a broken raw egg and said filtering means includes an optical filter disposed between said photoelectric receiver and the albumen.

9. A method for detecting rotten albumen in a raw egg, comprising the steps of:
   casting ultraviolet light onto albumen to be inspected, the albumen may include yolk material;
   using an optical system having a combination of a tinted glass filter and an interference filter for filtering a complex of fluorescence received from the albumen and ultraviolet light reflected from or transmitted through the albumen so as to transmit only the components due to fluorescence of the albumen;

receiving the fluorescence of the albumen and outputting a corresponding signal;

comparing the signal to a predetermined signal, the outputted signal corresponding to the level of the fluorescence of the albumen and the predetermined signal corresponding to a threshold level representing the fluorescence of sound albumen.

10. A method as recited in claim 9, wherein the filtering step is performed prior to the fluorescence receiving step.

11. A method as recited in claim 9, wherein the filtering step is performed so as to transmit only the wavelength band between approximately the upper limit of wavelength of ultraviolet light and approximately the lower limit of wavelength of fluorescence from sound yolk material.

* * * * *